United States Patent [19]

Glass

[11] Patent Number: 4,786,684
[45] Date of Patent: Nov. 22, 1988

[54] BENZYLTHIOETHER-LINKED SOLID SUPPORT-BOUND THIOL COMPOUNDS AND METHOD FOR PEPTIDE SYNTHESIS

[75] Inventor: John D. Glass, Shoreham, N.Y.

[73] Assignee: The Mount Sinai School of Medicine of the City University of New York, New York, N.Y.

[21] Appl. No.: 899,209

[22] Filed: Aug. 21, 1986

[51] Int. Cl.$^4$ .................. A61K 37/02; C08F 36/06; C08F 136/06
[52] U.S. Cl. .................. 525/54.1; 525/333.2; 525/333.3; 526/336; 530/334; 530/336; 424/85.8; 424/88
[58] Field of Search .............. 530/333, 334, 336; 525/54.1, 54.11, 333.2, 333.3; 526/336; 424/85, 88

[56] References Cited

U.S. PATENT DOCUMENTS 3,743,628  7/1973  Bodanszky et al. .............. 525/54.1
4,193,915  3/1980  McKerns .............. 530/334

OTHER PUBLICATIONS

*Molecular and Cellular Regulation of Enzyme Activity*, pp. 74–75, Second International Meeting, Martin-Luther-University Halle-Wittenberg, Aug. 17–23, 1986, GDR, Editors: Gerhard Hubner, Hans Possin.
"The Proteins", 3rd Edition, vol. II, *Academic Press*, Hans Neurath, Robert L. Hill, Assisted by Carol-Leigh Boeder, 1976.
"Tissue Sulfhydryl Groups", George L. Ellman, *Archives of Biochemistry and Biophysics*, 82, pp. 70–77 (1959).
"Structural and Conformational Considerations: Enkephalins", Peter W. Schiller & John DiMaio, *Proc. 8th American Peptide Symp.*, pp. 269–278.
*Anal. Biochem.*, vol. 34, pp. 595–598, 1970, "Color Test for Detection of Free Terminal Amino Groups in the Solid-Phase Synthesis of Peptides".
"N-Hydroxyverbindungen als Katalysatoren fur die Aminolyse aktivierter Ester", Wolfgang Konig and Rolf Geiger, *Chem. Ber.*, 106, pp. 3626–3635, 1973.
*The Journal of Biological Chemistry*, vol. 237, No. 5, May 1962, pp. 1563–1566, Hope, Murti and Du Vigneaud.
"Bidirectional Solid-Phase Peptide Synthesis, Extension of the Dinitrophenylene-Bridging Method to Cysteine-Containing Peptides", John D. Glass, A. Talansky, Z. Grzonka, I. L. Schwartz, and Roderich Walter et al., *Journal of the American Chemical Society*, 96:20, Oct. 2, 1974.

Primary Examiner—John Kight
Assistant Examiner—Nathan M. Nutter
Attorney, Agent, or Firm—Brumbaugh, Graves, Donohue & Raymond

[57] ABSTRACT

A method for the synthesis of sulfydryl-containing peptides which comprises forming a benzylthioether-linked solid support-bound thiol compound having at least one functional group for generating at least one peptide bond, sequentially coupling at least one protected amino acid or peptide to the compound until a peptide having desired amino acid sequence is obtained, and cleaving the benzylthioether linkage to release the peptide from the support with concomitant regenertion of the sulfydryl group in the peptides. The invention also encompasses compounds having the general formula

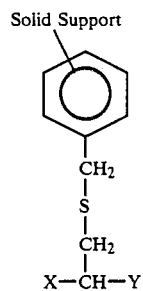

wherein X is H, NH$_2$,

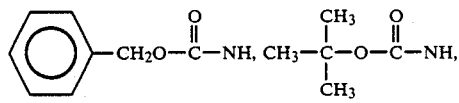

or acyl-NHY, said acyl being an amino acid or a peptide; Y is H, COOH, CONHNH$_2$,

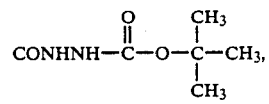

the ester COOR$^1$ in which R$^1$ is selected from the group consisting of methyl, ethyl, phenyl, ortho-nitrophenyl and para-nitrophenyl, the amide CONH$_2$, or the amide CONHR$^2$ in which R$^2$ is an amino acid or peptide; and providing that X and Y cannot both be H.

19 Claims, No Drawings

BENZYLTHIOETHER-LINKED SOLID SUPPORT-BOUND THIOL COMPOUNDS AND METHOD FOR PEPTIDE SYNTHESIS

BACKGROUND OF THE INVENTION

The present invention relates to a method for synthesis of sulfhydryl-containing peptides which comprises forming a benzylthioether-linked solid support-bound thiol compound, coupling at least one amino acid or peptide to said compound until a peptide of desired amino acid sequence is obtained, and cleaving the benzylthioether linkage to release the synthesized peptide from the support with concomitant regeneration of the sulfhydryl group in the peptide. The invention also relates to novel solid support-bound thiol compounds and their use for introducing sulfhydryl groups into peptides, particularly antigens and pharmaceutical peptides.

Several methods are known wherein peptides are synthesized in vitro. The principal methodology used for peptide synthesis involves variations of the solid-phase methodology developed by Merrifield and coworkers; see, for example, Erickson and Merrifield, "The Proteins", Third Edit., Vol. 2, Academic Press, New York, Chapter 3, (1976). Solid phase peptide synthesis involves attachment of a first amino acid to a solid support, such as a resin, followed by sequential addition of subsequent amino acids which results in assembly of the peptide chain on the solid support.

Peptides can also be synthesized by related methods involving coupling peptide fragments to solid supports as discussed by Erickson et al., suora, pp. 268-269. This technique involves the synthesis of small peptide segments containing a few amino acids, which segments are then coupled to each other using fragment condensation techniques to form larger peptides. Fragment condensation techniques can be combined with standard solid phase techniques wherein small peptides are attached to resins followed by sequential attachment of single amino acids or other peptide segments. Alternatively, sequential attachment of small peptides to single resin-bound amino acids can also be accomplished. The combination of the two approaches provides flexibility to synthetic schemes.

Upon completion of a particular synthesis, the synthesized peptide is then removed from the resin, usually by chemical means such as treatment with hydrofluoric acid (HF). The chemical treatment also removes various amino acid and peptide protecting groups, such as CBZ, t-Boc or Tosyl, which mask the reactivity of amino acid functional groups during synthesis.

In most peptide syntheses, the initial attachment to the resin involves the C-terminal amino acid of the peptide to be synthesized, which amino acid is covalently attached to the resin through an ester or amide linkage involving its α-carboxyl group. Synthesis then proceeds from C- to N-terminal. N-terminal to C-terminal peptide synthesis is less frequently used because the chemistry is more difficult and unwanted side reactions are more common.

The first amino acid may be covalently attached to the resin, in some cases, through its functional side chain. Initial attachment of an amino acid to the resin by means of the side chain functional group allows the possibility of bidirectional synthesis starting with the attached amino acid. Bidirectional synthesis cannot be performed if the initial amino acid is attached through the α-COOH or α-NH₂ group. Side chain functional groups which have been used for attachment to resins include the sulfhydryl group of cysteine, the imidazole group of histidine, the δ-amino group of ornithine, the ε-amino group of lysine and the γ-carboxyl group of glutamic acid. A review of the chemistry of solid phase peptide synthesis, including attachment of amino acids to resins via the α-COOH, α-NH and functional side chain groups, is found in Erickson et al., supra.

One particular example of an amino acid attachment via a functional side chain is the S-dinitrophenylene bridge between the side chain of cysteine and the support resin described by Glass et al., J. Amer. Chem. Soc. Vol. 96, pp. 6476-6480 (1974). This bridge involves a thioether linkage between the peptide and the resin which was stable to acidolysis but cleavable by thiolysis. Resin-bound cysteine, attached via the S-dinitrophenylene bridge has been used for bidirectional solid phase peptide synthesis wherein the peptide chains were extended from the attached cysteine toward both the N- and C-termini of the synthesized peptide. The peptides, therefore, had an internal cysteine.

The thioether S-dinitrophenylene bridge, however, has not been extensively used in peptide synthesis because it undergoes undesirable side reactions in the presence of base. Chemical steps commonly used in solid phase peptide synthesis cannot be used with the S-dinitrophenylene thioether-linked cysteine. Extensive reagent modification and great care are needed to minimize adverse side reactions.

Benzyl and substituted benzyl groups are known as removable protection groups which mask the reactivity of the sulfhydryl group of cysteine during peptide synthesis. An example of such use is provided in U.S. Pat. No. 3,743,628 which describes the synthesis of t-Butyloxycarbonyl-S-benzyl-L-cysteine. These protecting groups are removable by acidolysis in anhydrous HF. As discussed in Erickson et al., sucra, electron donating groups, such as methyl or methoxyl moieties, in the ortho and para positions of the benzyl group are known to increase the rate of HF cleavage. On the other hand, electron withdrawing groups in the ortho or para positions are known to decrease HF sensitivity. Other methods of cleaving S-benzyl and substituted S-benzyl groups, such as sodium in anhydrous ammonia or hydrogenolysis in anhydrous ammonia are known, but such methods are unsuitable for removing peptides bound to resins.

The introduction of thiol groups into biologically and pharmaceutically important peptides can have significant impact on the specific properties and activity of such compounds. Several naturally occurring semi-rigid cyclic peptides are known in nature. However, the majority of biologically active peptides, such as peptide hormones and neurotransmitters, are linear and flexible. In some instances conformational flexibility of such peptides gives rise to an observed lack of receptor binding specificity. Decreasing the conformational flexibility of peptide hormones and neurotransmitters provides a means to enhance biological and pharmacologic properties, such as increased receptor binding capacity and specificity.

Schiller et al., Proceedings of the Eighth American Peptide Symposium, pp. 269-278, Pierce Chemicals, 1983, discussed various means to obtain peptides with conformational restrictions. One approach is the synthesis of peptide analogs containing cyclic structures.

The incorporation of sulfhydryl groups into peptides allows cyclization of small regions of the peptide through disulfide bonds produced by oxidation of the free sulfhydryl groups. In addition, thioether bonds formed by reacting a sulfhydryl group with an active akylating group introduced into an amino acid side chain may also be used to generate a cyclic structure. Peptides containing loop structures have decreased conformational freedom when compared to the corresponding linear analog.

As discussed above, such a change in conformational freedom may also be associated with a change in reactivity of the peptide. Synthesis of peptide analogs containing an intramolecular loop may also alter the susceptibility of the peptide to degradation by proteolysis. For example, peptide bonds which are substrates for proteases when present in a linear peptide sequence may become poor substrates for the same proteases when the peptide bonds lie within a small disulfide loop.

The effects of the introduction of such cyclic structures on conformational rigidity and resistance to proteolysis, therefore, can provide desirable biologic and pharmacologic properties to cyclic peptide derivatives as compared to acyclic peptides. Disulfide loops may thus be introduced into pharmaceutically useful analogs of biologically active peptides which, in their native state, do not contain such loops. (See, for example, Schiller et al., supra).

The introduction of thiol compounds into peptide sequences also provides a convenient chemical handle for further manipulation of the sulfhydryl-containing peptide. Because of their chemical reactivity such sulfhydryl groups can provide a means of covalently linking a peptide to other molecules or peptides. For example, a technique for producing antibodies to a small synthetic peptide antigen, which ordinarily would not elicit antibody production, is to conjugate the peptide to a large carrier protein such as keyhole limpet hemocyanin or bovine serum albumin. The conjugate is then used to elicit antibodies in a suitable host. One method of preparing such immunogenic conjugates is to synthesize a peptide containing a cysteine at one end. When the cysteine-containing peptide is mixed with a hemocyanin derivative containing maleimide groups, the peptide becomes covalently attached through the cysteine sulfhydryl group to the carrier protein.

According to the present invention, a new method has been found which allows the synthesis of peptides containing useful sulfhydryl groups. The method makes use of novel reagents in which thiol compounds have been attached to solid supports through a cleavable benzylthioether linkage.

DESCRIPTION OF THE INVENTION

The present invention relates to a method for synthesis of sulfhydryl containing peptides. The method comprises a first step of forming a benzylthioether-linked solid support-bound thiol compound. As a second step, at least one protected amino acid or peptide is sequentially coupled to the compound, the coupling proceeding until a peptide having a desired amino acid sequence is obtained. Upon completion of peptide synthesis, as a third step, the benzylthioether linkage is cleaved, thus releasing the synthesized peptide from the support with concomitant regeneration of the sulfhydryl group in the peptide. Furthermore, the thiol compounds of the present invention must have at least one functional group therein for generating the formation of at least one peptide bond.

The invention also encompasses compounds having the general formula

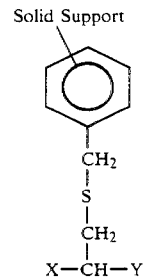

wherein X is H, $NH_2$,

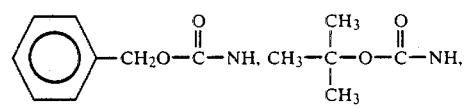

or acyl-NH, said acyl being an amino acid or a peptide; Y is H, COOH, $CONHNH_2$,

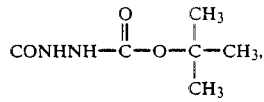

the ester $COOR^1$ in which $R^1$ is selected from the group consisting of methyl, ethyl, phenyl, ortho-nitrophenyl and para-nitrophenyl, the amide $CONH_2$, or the amide $CONHR^2$ in which $R^2$ is an amino acid or peptide; and providing that X and Y cannot both be H.

Peptide synthesis using such compounds involves known solid phase techniques in which protected amino acids or protected peptides are sequentially added to a growing peptide chain until a desired sequence is obtainable. The benzylthioether linkage of the compounds of the invention is cleavable by agents, such as hydrofluoric acid, known to cleave peptides from solid supports and also remove amino acid side chain protecting groups. The cleavage of peptides synthesized on the compounds of the invention concomitantly regenerates the sulfhydryl group in the synthesized peptide. The above compounds permit the synthesis of sulfhydryl containing peptides which are not readily synthesized by present techniques. For example, the synthesis of peptides containing a C-terminal cysteamine is extremely difficult with the standard C- to N-terminal synthesis format, since cysteamine has no α-COOH group to attach to the resin. The present invention readily allows synthesis of peptides with a C-terminal cysteamine.

The solid support-bound thiol compounds having the above general formula form part of the present invention. Such compounds are prepared by reacting, in the presence of a tertiary amine, the free thiol compound with a solid support material having covalently attached thereto reactive benzyl groups. Preferably, such benzyl groups should contain electron donating groups in the ortho or para positions to facilitate cleavage of the benzylthioether bond. Preferred tertiary amines include triethylamine and diisopropylethylamine, although peptide synthesis chemists would recognize that other such compounds are equally suitable. The coupling reaction, which proceeds overnight at room temperature, and subsequent wash steps yield products suitable for peptide synthesis by known solid phase techniques involving successive addition of protected amino acids or protected peptide fragments.

The solid supports of the present invention can be any material containing a benzyl halide group conventionally employed in solid phase synthesis. Cleavage by hydrofluoric acid or other such agents is facilitated by the presence of an electron donating moiety in the ortho or para positions. Solid supports useful in accordance with the invention are described in Erickson et al., supra, and include but are not limited to resins, such as chloromethylated phenol-formaldehyde polymers and chloromethylated copolymers of 2-hydroxyethyl methacrylate/ethlenedimethacrylate/methacrylanilide, and silicates, such as α-chlorobenzyl derivatized porous glass beads and α-bromobenzyl derivatized porous glass beads. The preferred solid support materials of the present invention are the chloromethylated copolystyrene/divinylbenze resins containing divinylbezene cross-links in the range of 0.5%–2% (Merrifield resins). The 1% cross-linked chloromethylated copolystyrene/divinylbenzene resin in bead form having a particle size in the 100–200 U.S. mesh range is particularly preferred. The resin may be readily utilized in the bead form obtained from a commercial source such as Pierce Chemicals.

In accordance with the present invention, thiol compounds attached by a benzylthioether linkage to 1% crosslinked chloromethylated copolystyrene/divinylbenzene resins have been prepared. Compounds having the following formulae are preferred:

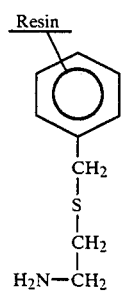

Compound I.

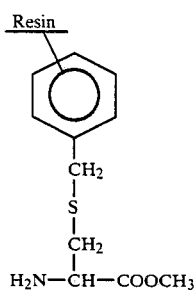

Compound II.

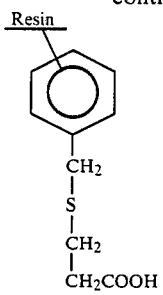

Compound III.

The benzylthioether-linked solid support-bound compounds of the presesnt invention allow bidirectional synthesis of peptides, thus resulting in peptides containing an internal sulfhydryl group. Also, the benzylthioether linkage to the resin is particularly suited for use in peptide synthesis since it is more stable to acidolysis than conventional ester or amide attachments.

The present invention also allows the synthesis of peptides and peptide analogs containing loop structures or cyclic regions. After peptide synthesis is completed, the benzylthioether bond is cleaved and the peptide is removed from the resin with regeneration of the sulfhydryl group in the peptide. If desired, peptides having cyclic regions are prepared by oxidation of two sulfhydryl groups introduced into the same peptide chain to cause formation of disulfide linkages bridging a small peptide loop. Alternatively, a loop can be formed through the incorporation of a thioether linkage into the peptide. The thioether bond is introducible into the synthesized peptide by reacting free sulfhydryl groups in the synthesized peptide with an active alkyl group attached to an $N^\alpha$-moiety or side chain of an amino acid or peptide. The thioether bond links the amino acid or peptide to the synthesized peptide. Such thioether linkages then permit formation of a loop structure in the synthesized peptide.

Also, under appropriate conditions, sulfhydryl groups in two different peptide chains are oxidizable to interchain disulfide bridges covalently linking the two peptides together.

A particular advantage of the present invention is the ability to synthesize peptides in which the N-terminus or C-terminus is a free sulfydryl group. For example, the cysteamine-resin, (compound I, above) permits synthesis of peptides having a C-terminal sulfhydryl group. β-Mercaptopropionic acid-resin (compound III) can be used in the synthesis of peptides with an N-terminal sulfhydryl group. Such terminal sulfhydryl group readily allows the attachment of the synthesized peptides containing the terminal sulfhydryl group to other molecules, such as proteins.

This particular advantage of the present invention provides a means of producing useful antibody reagents to the peptides. Peptides having an N- or C- terminal sulfhydryl group are synthesized. Such peptides are then conjugated to a carrier protein. For example, peptides containing a C-terminal free sulhydryl group obtained by synthesis on the cysteamine-resin is conjugatable through the free sulhydryl group to a large carrier protein by known techniques. The β-mercaptopropionic acid-resin provides peptides containing an N-terminal free sulfhydryl group through which the peptide is conjugated to a carrier protein. Whereas immunization of a suitable host with the free peptide elicits a poor antibody response, immunization with the conjugate produces an excellent antibody responee to the peptide.

It will be thus recognized by those skilled in the art that the present invention is useful for synthesis of peptides not well accommodated by present peptide synthesis techniques. Peptides, which are encompassed by the present invention, include biologically and pharmaceutically useful peptides and peptide analogs containing therein intramolecular disulfide bonds or thioether linkages which bridge cyclic regions or intermolecular disulfide bonds which attach one peptide to another. Such peptides and peptide analogs include those derived from the sequence of human plasmin at its active site.

In addition, synthetic peptide antigens containing an N- or C-terminal free sulfhydryl group permiting attachment to a carrier protein for the production of antibodies are also encompassed by the present invention. Accordingly, a peptide antigen reagent wherein a synthesized peptide containing a C-terminal cysteamine through which the peptide is conjugated to a carrier protein forms part of the present invention.

The invention is further described by the following examples:

EXAMPLE 1

Resin-Bound Cysteamine (Compound I, above)

A quantity of 5.6 g (50 millimoles) cysteamine hydrochloride and 20.9 ml (150 millimoles) triethylamine was added to a suspension of 5 g beaded (U.S. mesh 100–200) 1% cross-linked chloromethylated styrene/divinylbenzene copolymer resin in 50 ml dimethylformamide. This resin, a so-called Merrifield resin having a chloromethylation level of 0.5–1.5 meq. per gram resin, was obtained from Pierce Chemical Co. The mixture was shaken at room temperature for 15 hours after which time the resin containing cysteamine bound thereto was filtered off and successively washed on a suction filter with about 300 ml each of water, dimethylformamide, dimethylformamide/water (1:1 v/v) and absolute ethanol. The resulting resin-bound cysteamine, which was found to be ninhydrin positive by the method of Kaiser et al., Anal. Biochem. Vol. 34, pp. 595–598 (1970), was dried in vacuo at room temperature. The resin-bound cysteamine contained about 0.22–0.25 milliequivalents of cysteamine bound per gram of resin as estimated following amino acid analysis of the peptides synthesized in Examples 6 and 7.

EXAMPLE 2

Resin-Bound Cysteine Methyl Ester (Compound II)

The conditions of Example 1 were repeated except that an equimolar amount of cysteine methyl ester hydrochloride (50 mmoles) replaced cysteamine hydrochloride in the reaction. Methyl ester blocks the reactivity of the cysteine α-carboxyl group, and enhances solubility of the compound. The resulting ninhydrin-positive resin contained about 0.1 milliequivalents of bound cysteine methyl ester per gram of resin, estimated from amino acid analysis of the peptide synthesized in Example 8.

EXAMPLE 3

Resin-Bound β-Mercaptopropionic Acid (Compound III)

Preparation of resin-bound β-mercaptopropionic acid (β-MP) was accomplished using the conditions set forth in Example 1 with the substitution of 50 mmoles β-mercaptopropionic acid for cysteamine hydrochloride. Subsequent determination of β-MP carboxyl group substitution indicated that the resin contained at least 0.08 milliequivalents of thioether bound thiol per gram of resin.

EXAMPLE 4

Solid-phase Synthesis of Peptides Using Thiol Compounds Attached to Resins Containing Benzylthioether-Linkages This example describes the peptide synthesis procedures by which protected amino acids and protected peptides were coupled to the benzylthioether-linked resin-bound thiol compounds of the invention to form peptides. The representative peptides described in subsequent Examples 5–9 were synthesized on the benzylthioether-linked resin-bound thiol compounds using the general solid phase techniques outlined by Erickson et al., supra, pp. 259–269. The specific conditions used in each instance are given in the Examples and in Tables I and II below. The peptides synthesized in the examples each have amino acid sequences analogous to a sequence of a portion of human plasmin at its active site.

Synthesis of the sulfydryl-containing peptides began with the preparation of the benzylthioether-linked resin-bound thiol compounds as described in the previous Examples. Boc-amino acids or appropriately protected peptide fragments were then coupled to the compound stepwise using the solid phase synthesis format. The coupling of single amino acids in combination with the coupling of peptide fragments provided greater flexibility to the synthetic schemes.

Briefly, elaboration of the peptide was accomplished by repetitive cycles, in which a Boc-amino acid or protected peptide was added to the benzylthioether-linked resin-bound thiol compounds of the invention; the blocking group on the α-NH$_2$ group of the first added amino acid or peptide or any subsequent added amino acid or peptide in the growing chain was removed, usually by mild acid cleavage (deprotection step); the α-NH$_2$ group was then converted to a base under the action of a tertiary amine (neutralization step); and finally the amino acid or peptide on the resin was acylated by an activated α-COOH group of a subsequent α-NH$_2$ protected amino acid or peptide (coupling step). Various solvent washing cycles necessary to remove excess reactants and reactant by-products were interspersed among the three basic steps (deprotection, neutralization, and coupling) of the peptide elongation process. The peptide chain was extended by such repetitive cycles until the peptide reached the desired length and sequence of amino acids.

The peptide chain was then cleaved from the resin with hydrofluoric acid (HF) which also removes chemical blocking groups, from the side chains of amino acids in the peptide. HF cleavage of the benzylthioether linkage by which the peptide was attached to the resin regenerated the free sulfydryl in the peptide. In Examples 5–8, subsequent oxidation, under appropriate conditions, generated an intermolecular (Example 5) or intramolecular (Examples 6–8) disulfide bond. Alternatively, as provided in Example 9, alkylation of the sulfhydryl group by a reactive alkyl halide attached to the N$^α$-moiety or side chain of an amino acid or peptide yielded a peptide thioether derivative.

Examples 5 and 9 disclose synthesis of peptides containing an N-terminal $NO_2$-Z-Arg-moiety. As provided in U.S. patent application Ser. No. 876,679 filed June 20, 1986, the Examples 5 and 9 peptides containing $NO_2$-Z-Arg were produced by the addition of $NO_2$-Z-Arg(Tos)-OH, synthesized as follows:

Synthesis of $NO_2$-Z-Arg(Tos)-OH

Boc-Arg(Tos)-OH, obtained from Bachem Fine Chemicals Co., Torrance, CA., was treated with trifluoracetic acid (Tfa) to remove the Boc group from the $\alpha$-$NH_2$ moiety. resulting $N^G$-p-toluenesulfonyl-L-arginine was treated with p-nitrobenzylchloroformate under known Shotten-Bowman conditions as follows. $N^G$p-toluenesulfonyl-L-arginine (0.05 moles as Tfa salt) was dissolved at 0° C. in 20 milliliters of 1M NaOH and 50 milliliters of dioxane. The pH of the solution was adjusted to between 11.2 and 11.5 (pH meter with glass electrode) and maintained within that range by addition of 1M NaOH as 0.05 moles of p-nitrobenzylchloroformate was added slowly. After the mixture stirred for 40 minutes, the pH remained constant at 11.5. The dioxane was removed from the reaction mixture by rotary evaporation and the remaining aqueous solution was extracted twice with equal volumes of ethyl acetate. The pH of the aqueous solution was then adjusted to about 3 with HCl, and then further extracted five more times with ethyl acetate. The ethyl acetate extracts of the acidified aqueous solution were then combined and dried over magnesium sulfate. The ethyl acetate was removed by rotary evaporation leaving a yellow oil, which was dissolved in acetone. $NO_2$-Z-Arg(Tos)-OH was crystallized from the acetone in 67% of the theoretical yield.

The arginine derivative so obtained was characterized by elemental analysis, NMR spectroscopy, melting point, and mobility in thin layer chromatography (TLC).

The elemental analysis was determined for $NO_2$-Z-Arg(Tos)-OH ($C_{21}H_{25}N_5O_8S$). The expected elemental composition (weight %) for carbon, hydrogen, and oxygen was calculated from the structure of $NO_2$-Z-Arg(Tos)-OH. The observed elemental composition values for carbon, hydrogen and nitrogen were then determined in two separate experiments. The expected and observed values (w %) are:

| Element | Expt. 1 | Expt. 2 | Expected |
|---------|---------|---------|----------|
| C | 49.46 | 49.45 | 49.70 |
| H | 4.92 | 4.94 | 4.97 |
| N | 13.36 | 13.48 | 13.80 |

The structure of $NO_2$-Z-Arg(Tos)-OH was further confirmed by a 100 megahertz proton magnetic resonance spectrum in which the 8 aromatic protons, the two methylene protons of the benzyl group, the 3 protons of the methyl group in the tosyl moiety, and the 8 protons of the aliphatic methylene groups were all accounted for in the expected regions of the spectrogram. The NMR analysis, therefore, was consistent with the proposed structure of the arginine derivative of the present invention.

$NO_2$-Z-Arg(Tos)-OH has a melting point of 122°–124° C.

$NO_2$-Z-Arg(Tos)-OH was analyzed by TLC on silica gel G plates in three different solvents. The mobilities of the compound relative to the solvent ($R_f$) were determined as:

| Solvent | $R_f$ |
|---------|-------|
| Methanol:Ethyl acetate; 4:1 | 0.68 |
| N—butanol:Acetic acid:Water; 4:1:1 | 0.71 |
| Chloroform:Methanol:Water; 65:25:4 | 0.89 |

$NO_2$-Arg(Tos)-OH was added to the peptides through the action of dicyclohexylcarbodiimide and 1-hydroxybenzotriazole and $NO_2$-Z-Arg(Tos)-OH as described by Koenig et al., Chem. Ber. Vol. 106, pp. 3626-3635 (1973) as the final cycle in the peptide chain assembly.

The amino terminal $NO_2$-Z groups, which resisted cleavage by HF, remained in the peptides of Examples 5 and 9 as a convenient chromophore and chromatographic handle for the subsequent isolation and detection of peptides containing this arginine derivative at their amino termini.

The particular steps of the solid phase peptide synthesis of the peptides described in Examples 5–9 are outlined in Tables I and II below. In Table I, step 1 is a wash step which swells the resin, steps 2 and 3 are deblocking steps, steps 4–6 are washes, step 7 is the neutralization step, step 8 is a wash, steps 9 and 10 are coupling steps; and steps 11–15 are washes. Table II outlines the synthetic scheme utilized to couple Boc-Glutamine, Boc-Asparagine, Boc-Arginine (Tosyl)-OH, $NO_2$-Z-Arg(Tos)-OH, and Boc- or CBZ-protected peptides to a growing peptide sequence on the support. Steps 1–8 in Table II are identical to those provided in Table I. Steps 9–11 are additional washing steps, steps 12–13 are coupling steps, and steps 14–19 are wash steps.

TABLE I

Coupling Schemes for Boc—Amino Acid Residues Other Than Boc—Asparagine, Boc—Glutamine and Boc—Arginine

| Con-di-tions Step | Reagent | Reaction Vol. (ml) | Duration (min.) | Number of Repetitions |
|---|---|---|---|---|
| 1 | Dichloromethane | 50 | 0.5 | 5 |
| $2^a$ | 50% Trifluoroacetic acid in dichloromethane or 33% HBr in acetic acid | 50 | 2.0 | 1 |
| $3^b$ | 50% Trifluoroacetic acid in dichloromethane or 33% HBr in acetic acid | 50 | 30.0/60.0 | 1 |
| 4 | Dichloromethane | 50 | 0.5 | 5 |
| 5 | 2-Propanol | 35 | 0.5 | 2 |
| 6 | Dichloromethane | 50 | 0.5 | 5 |
| 7 | 5% Diisopropylethylamine in dichloromethane | 35 | 2.0 | 3 |
| 8 | Dichloromethane | 50 | 0.5 | 5 |
| $9^c$ | Boc—Amino Acid derivative in dichloromethane | 15 | 2.0 | 1 |
| 10 | Dicyclohexylcarbodiimide (DCC) in dichloromethane | 15 | 30.0 | 1 |
| 11 | Dichloromethane | 50 | 0.5 | 5 |
| 12 | 2-Propanol | 35 | 0.5 | 2 |
| 13 | Dichloromethane | 50 | 0.5 | 2 |
| 14 | 2-Propanol | 35 | 0.5 | 2 |

TABLE I-continued

Coupling Schemes for Boc—Amino Acid Residues Other Than Boc—Asparagine, Boc—Glutamine and Boc—Arginine

| Conditions Step | Reagent | Reaction Vol. (ml) | Duration (min.) | Number of Repetitions |
|---|---|---|---|---|
| 15 | Dichloromethane | 50 | 0.5 | 5 |

[a]50% Tfa is used to remove Boc-protecting groups from amino acids or peptides bound to the resin.
33% HBr in acetic acid ($CH_3COOH$) is used to remove CBZ protecting groups from peptides bound to the resin.
[b]Tfa - 30 min. to remove Boc-groups $HBr/CH_3COOH$ - 60 min. to remove CBZ-groups.
[c]After step 15, the resin is checked for completeness of coupling by the ninhydrin method of Kaiser et al., Anal. Biochem., vol. 34, pp. 595-598 (1970). If the reaction is incomplete (i.e. positive ninhydrin test) steps 9-15 are repeated.
Boc amino acids and dicyclohexylcarbodiimide are used in 3 fold molar excess compared to the amino groups available on the peptide-resin derivative.

TABLE II

Coupling Schemes for Boc—Glutamine, Boc—Asparagine, Boc—Arg(Tos)—OH, $NO_2$—Z—Arg(Tos)—OH and Boc—and CBZ—peptides

| Step | | Reaction Conditions Vol. (ml) | Duration (min.) | Repetitions |
|---|---|---|---|---|
| 1-8 | are identical with those of Table I | | | |
| 9 | 2-Propanol | 35 | 0.5 | 2 |
| 10 | Dichloromethane | 50 | 0.5 | 5 |
| 11[a] | Dimethylformamide | 35 | 2.0 | 3 |
| 12[b] | Protected Amino Acid or $N^\alpha$-Protected Peptide*/HOBzt/DMF | 15 | 2.0 | 1 |
| 13 | Dicyclohexyl carbodiimide (DCC) in dimethylformamide* | 15 | 120.0 | 1 |
| 14 | Dimethylformamide | 35 | 0.2 | 1 |
| 15 | Dichloromethane | 50 | 0.5 | 5 |
| 16 | 2-Propanol | 35 | 0.5 | 2 |
| 17 | Dichloromethane | 50 | 0.5 | 2 |
| 18 | 2-Propanol | 35 | 0.5 | 2 |
| 19 | Dichloromethane | 50 | 0.5 | 5 |

[a]Amino acid derivatives and dicyclohexylcarbodiimide are used in 3 fold molar excess compared to the amino groups available on the peptide resin derivatives.
[b]1-Hydroxybenzotriazole hydrate (HOBzt) is used in 2 fold molar excess compared to the amino acid derivatives. HOBzt, as described by Koenig et al., Chem. Ber. vol. 106, pp. 3626-3635 (1973), is used to prevent unwanted side reactions.
*In coupling schemes involving $N^\alpha$-protected peptide-nitrophenyl (ONp) esters and $N^\alpha$-protected peptide-pentachlorophenyl (OPcp) esters steps 12 and 13 are combined. $N^\alpha$-protected peptide-ester is substituted for protected amino acid, HOBzt and DCC.

EXAMPLE 5

Synthesis of ($NO_2$-Z-Arg-Val-Gly-Gly-NH-$CH_2$-$CH_2$-S-)$_2$

Boc-Gly-Gly-OH and Boc-Val-OH were sequentially coupled to the resin-bound cysteamine (Cya) made in Example 1 using the solid phase synthetic format provided in Tables I and II until the intermediate Boc-Val-Gly-Gly-NH-$CH_2$-$CH_2$-S-Resin was obtained. The intermediate was deprotected with trifluoroacetic acid and neutralized with diisopropylamine. Following the procedure in Table II, $NO_2$-Z-Arg(Tos)-OH prepared according to Example 1 of application Ser. No. 876,679 was coupled to the Val-Gly-Gly-NH-$CH_2$-$CH_2$-S-Resin by the action of dicyclohexylcarbodiimide in the presence of 1-hydroxybenzotriazole to provide $NO_2$-Z-Arg-Val-Gly-Gly-NH-$CH_2$-$CH_2$-S-Resin.

Amino acid analysis of this resin bound peptide following treatment with 3N HCl in Propionic acid (Pierce Chemical Co.) for 22 hours at 110° C. gave the following results:

| Amino Acid | Observed Value | (Expected Value) |
|---|---|---|
| Arg | 1.0 | (1.0) |
| Val | 1.2 | (1.0) |
| Gly | 1.7 | (2.0) |

Treatment of $NO_2$-Z-Arg-Val-Gly-Gly-NH-$CH_2$-$CH_2$-S-Resin with anhydrous HF at 0° C. for an hour yielded $NO_2$-Z-Arg-Val-Gly-Gly-NH-$CH_2$-$CH_2$-SH. This soluble intermediate sulhydryl-containing peptide, which gave a positive test for thiols as provided by Ellman, Archives Biochem. Biophys., Vol. 82, pp. 70-77 (1959), was subsequently oxidized by aeration at pH 9. The resulting product, ($NO_2$-Z-Arg-Val-Gly-Gly-NH-$CH_2$-$CH_2$-S-)$_2$, precipitated from solution.

Amino acid analysis of this disulfide-containing dimeric peptide following performic acid oxidation which converts cysteamine to taurine followed by acid hydrolysis (6N HCl, 22 hours., 110° C.) yielded:

| Amino Acid | Observed Value | (Expected Value) |
|---|---|---|
| Taurine | 1.1 | (1.0) |
| Gly | 2.3 | (2.0) |
| Val | 0.8 | (1.0) |
| Arg | 0.7 | (1.0) |

The synthetic steps described above are summarized in the following schematic representation of the synthesis of ($NO_2$-Z-Arg-Val-Gly-Gly-NH-$CH_2$-$CH_2$-S-)$_2$:

Synthetic Scheme for
($NO_2$—Z—Arg—Val—Gly—Gly—NH—$CH_2$—$CH_2$—S—)$_2$ $H_2N$—$CH_2$—$CH_2$—S—Resin     (Example 1)

↓ Boc—Gly—Gly—OH/dcc/HOBzt     (Table II)

Boc—Gly—Gly—Cya—Resin

↓ 1. Tfa
2. Diisopropylethylamine     (Table I)
3. Boc—Val—OH/dcc

Boc—Val—Gly—Gly—Cya—Resin

↓ 1. Tfa
2. Diisopropylethylamine     (Table II)
3. $NO_2$—Z—Arg(Tos)—OH/dcc/HOBzt $NO_2$—Z—Arg(Tos)—Val—Gly—Gly—Cya—Resin ↓ 1. HF
2. air oxidation ($NO_2$—Z—Arg—Val—Gly—Gly7—NH—$CH_2$—$CH_2$—S—)$_2$

EXAMPLE 6

Synthesis of 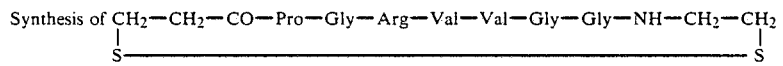

Resin-bound cysteamine, prepared according to Example 1, was acylated successively with Boc-Val-Val-Gly-Gly-OH, Boc-Arg(Tos)-OH and Z-Pro-Gly-OPcp as described in Tables I and II.

Boc-Arg(Tos)-OH was obtained from Bachem Fine Chemical Co., Torrance, CA.

Boc-Val-Val-Gly-Gly-OH was synthesized as follows:

Glycylglycine ethyl ester hydrochloride (Sigma Chemical Co. #G 3129) was neutralized with one equivalent of triethylamine, then coupled to Boc-valine via its mixed anhydride with isobutylcarbonic acid. The resultant Boc-Val-Gly-Gly-OEt was treated with trifluoroacetic acid to remove the Boc group, then another residue of Boc-valine was added to the peptide chain by the mixed anhydride method. The Boc-Val-Val-Gly-Gly-OEt intermediate was isolated as a crystalline product and characterized by analysis for carbon, hydrogen, and nitrogen composition.

Calculated for $C_{21} H_{38} N_4 O_7$; C:55.00; H:835; N:12.22. Found: C:54.99; H:8.41; N:12.27.

The ethyl ester was saponified with KOH in aqueous methanol to yield Boc-Val-Val-Gly-Gly-O$^-$K$^+$ which converted to Boc-Val-Val-Gly-Gly-OH by careful acidification to about pH 3.

Z-Pro-Gly-OPcp was prepared as follows:

Z-Pro-OH was coupled to H-Gly-OEt by the mixed anhydride method. The ethyl ester group was removed by saponification, and Z-Pro-Gly-OH (not isolated or characterized) was coupled to pentachlorophenol by the action of dicyclohexylcarbodiimide. The product was crystallized from ethanol or isopropanol and analyzed for C,H,N composition.

Calculated for $C_{21} H_{17} Cl_5 N_2 O_5$; C:45.47; H:3.09; N:5.05. Found: C:45.67; H:3.38; N:4.84. β-mercaptopropionic acid (Meb) was added as the last step in the synthesis to yield the intermediate product MP(Meb)-Pro-Gly-Arg(Tos)-Val-Gly-Gly-NH-CH$_2$-CH$_2$-S-Resin.

Amino acid analysis following treatment with 2N HCl in Propionic acid for 22 hours at 110° C. gave the following:

| Amino Acid | Observed Value | (Expected Value) |
|---|---|---|
| Pro | 0.9 | (1.0) |
| Gly | 3.1 | (3.0) |
| Val | 2.3 | (2.0) |
| Arg | 0.9 | (1.0) |

Calculation of the amount of peptide bound and recovered from the resin provided an estimate of 0.22 meq cysteamine bound per gram resin.

The peptide was cleaved from the resin with anhydrous HF at 0° for 1 hr. which produced a water soluble, Ellman positive product. Following oxidation with dilute aqueous potassium ferricyanide, the oxidized product was purified by reverse phase HPLC on a Vydac® C-18 peptide/protein column developed with 6% isopropanol/0.1% Tfa and hydrolyzed for 48 hours at 110° C. with 6N HCl. Amino acid analysis yielded:

| Amino Acid | Observed Value | (Expected Value) |
|---|---|---|
| Pro | 1.2 | (1.0) |
| Gly | 2.8 | (3.0) |
| Val | 1.95 | (2.0) |
| Arg | 1.2 | (1.0) |

The oxidized peptide was subjected to trypsin cleavage, followed by reversal of the trypsin hydrolysis reaction in the presence of a high concentration of 1,4 - butanediol. This series of reactions confirmed the intramolecular loop structure of the peptide.

The synthetic steps described above are summarized in the following schematic representation of the synthesis of this peptide:

Synthetic Scheme for 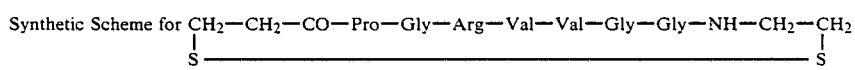

H—Cya—Resin  (Example 1)

↓ Boc—Val$_2$—Gly$_2$—OH/dcc/HOBzt  (Table II)

Boc—Val$_2$—Gly$_2$—Cya—Resin

↓ 1. trifluoroacetic acid
2. diisopropylethylamine
3. Boc—Arg(Tos)—OH/dcc/Hobzt  (Table II)

Boc—Arg(Tos)—Val$_2$—Gly$_2$—Cya—Resin

↓ 1. trifluoroacetic acid
2. diisopropylethylamine
3. Z—Pro—Gly—OPcp  (Table II)

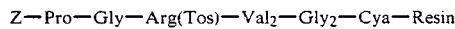

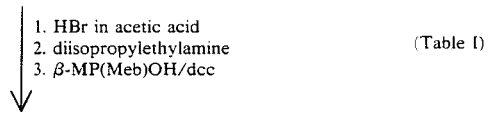   (Table I)

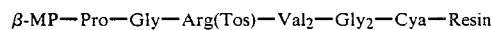

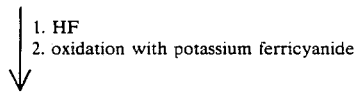

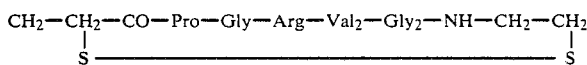

β-MP = β-mercaptopropionic acid
Meb = 4-methylbenzyl
Cya = cysteamine

EXAMPLE 7

Synthesis of 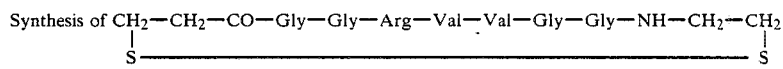

This peptide was synthesized, isolated, and characterized as described in Example 6 with the exception that a glycine residue was substituted for proline. This was accomplished by acylation with Z-Gly-Gly-ONp (purchased from Sigma Chemical Co.) in place of Z-Pro-Gly-OPcp in the previous Amino acid analysis of the peptide-resin intermediate provided:

| Amino Acid | Observed Value | (Expected Value) |
|---|---|---|
| Gly | 2.8 | (4.0) |
| Val | 2.1 | (2.0) |
| Arg | 1.0 | (1.0) |

The low glycine value probably resulted from incomplete hydrolysis of the peptide bound to the resin or partial destruction of glycine during hydrolysis. A calculation of the amount of peptide bound to the resin gave an estimate of 0.25 meq cysteamine bound per g resin.

Amino acid analysis following treatment of the free peptide with 6N HCl for 48 hours at 110° yielded:

| Amino Acid | Observed Value | (Expected Value) |
|---|---|---|
| Gly | 4.0 | (4.0) |
| Val | 1.7 | (2.0) |
| Arg | 1.0 | (1.0) |

The synthetic steps described above are summarized in the following schematic representation of the synthesis of this peptide:

Synthesis Scheme for 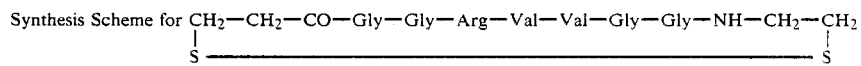

H—Cya—Resin   (Example 1)

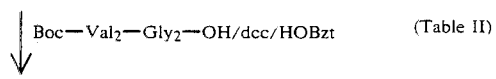   (Table II)

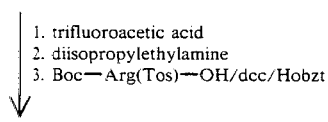   (Table II)

-continued

Boc—Arg(Tos)—Val₂—Gly₂—Cya—Resin

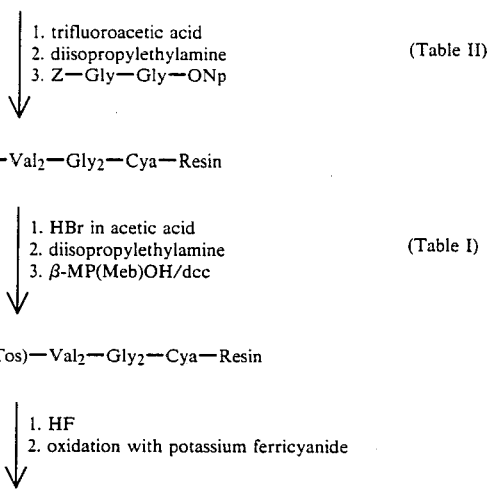

β-MP—Gly—Gly—Arg(Tos)—Val₂—Gly₂—Cya—Resin

| 1. HF
| 2. oxidation with potassium ferricyanide
↓

```
CH₂—CH₂—CO—Gly—Gly—Arg—Val₂—Gly₂—NH—CH₂—CH₂
 |                                                  |
 S——————————————————————————————————————————————————S
```

β-MP = β-mercaptopropionic acid
Meb = 4-methylbenzyl
Cya = cysteamine

EXAMPLE 8

Boc-Tyr-phe-Gln-Asn-Cys(OMe)-Resin

Resin-bound cysteine methyl ester, prepared according to Example 2, was successively acylated with amino acid derivatives by standard solid phase techniques as previously described. At each cycle of the synthesis an intermediate having a free amino group was produced which gave a positive ninhydrin reaction using the method of Kaiser. The peptide-resin intermediates became ninhydrin negative after each coupling reaction.

After the first cycle of solid phase synthesis, a sample of the dipeptide-resin intermediate was hydrolyzed for 22 hours at 110° C. in 3 HCl in propionic acid, with the resulting hydrolysate analyzed for aspartic acid. The quantity of aspartic acid in the hydrolysate corresponded to a substitution of approximately 0.1 milliequivalents of peptide per gram of resin.

EXAMPLE 9

NO₂-Z-Arg-Val-Gly-Gly-NH-CH₂-CH₂-S-CH₂-Gly-Gly-OH

NO₂-Z-Arg(Tos)-Val-Gly-Gly-Cya-Cya-Resin (1.5 g) was treated with anhydrous HF at 0° for one hour in the presence of anisole. The HF and anisole were evaporated under reduced pressure and the residual solids were washed with ether. The liberated peptide thiol was dissolved in 0.2 M acetic acid under nitrogen gas and the resin was removed by filtration. The aqueous acetic acid solution gave a strong Ellman test for thiols. Chloroacetylglycylglycine (500 mg) was added to the aqueous solution and the pH of the solution was adjusted to 8.5 with sodium hydroxide. Over a period of 1.5 hours, the Ellman reaction for thiols diminished to a very weak reaction. At the end of 2 hours the solution was negative to the Ellman test. The pH of the solution was adjusted to 3 with HCl and added to a (2.5×30 cm) column of AG 50W×2 (cation exchanger). Following a column wash with 0.2 M acetic acid (300 ml) and water (300 ml.), the product was eluted with a mixture of 90 ml pyridine and 12 ml acetic acid diluted to 300 ml with water. The eluate was evaporated to a gummy solid, 10 ml water was added, and the solution was filtered. Two ml were applied to a reversed phase C-18 HPLC column (Vydac ® peptide/protein column) in 0.1% Tfa. The column was then washed with 0.1% Tfa and the product was eluded with 7% isopropanol in 0.1% Tfa. A solution corresponding to the major elution peak monitored at 265 nm was frozen and lyophilized to yield 46 mg of white, cottony, hydroscopic solid.

Where it is desired to form a cyclic peptide, the NO₂-Z group is removed from the N-terminal Arg by mild reduction with dithionite in neutral aqueous solutions. Following removal of the NO₂-Z blocking group, a cyclic peptide is formed by coupling the free α-NH₂ group of Arg to the free α-COOH of the C-terminal glycine in the presence of dicyclohexylcarbociimide and 1-hydroxybenzotriazole (Tables I and II) or other known coupling methods. The coupling reaction produces a peptide bond formation between Arg and Gly, which in turn yields a cyclic peptide.

I claim:

1. In a method of synthesizing sulfhydryl-containing peptides, the improvement comprising
   (a) forming a benzylthioether-linked solid support-bound thiol compound, said thiol compound having at least one functional group for generating at least one peptide bond;
   (b) coupling to said thiol compound at least one protected amino acid or peptide to form a peptide of desired amino acid sequence; and
   (c) cleaving the peptide from the support at the benzylthioether linkage.

2. In a method of synthesizing sulfhydryl-containing peptides, the improvement comprising
   (a) forming a benzylhioether-linked solid support-bound thiol compound with the general formula

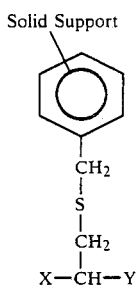

wherein X is H, NH₂,

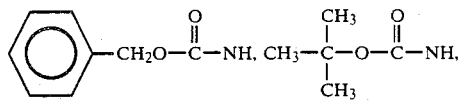

or acyl-NH, said acyl being an amino acid or a peptide;
Y is H, COOH, CONHNH₂,

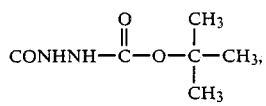

the ester COOR¹ in which R¹ is selected from the group consisting of methyl, ethyl, phenyl, ortho-nitrophenyl and para-nitrophenyl, the amide CONH₂, or the amide CONHR² in which R² is an amino acid or peptide; and providing that X and Y cannot both be H;

(b) coupling to said compound at least one protected amino acid or peptide to form the desired peptide sequence; and (c) cleaving the benzylthioether bond to liberate the synthesized peptide from the resin with concomittant regeneration of the free sulfhydryl group in the peptide.

3. The method according to claim 1 wherein the synthesized peptide is cyclized by oxidizing sulfhydryl groups to form intramolecular disulfide bonds.

4. The method according to claim 1 wherein the synthesized peptide is covalently attached to a second peptide by oxidizing sulfhydryl groups to form intermolecular disulfide bonds.

5. The method according to claim 1 wherein a thioether bond is introduced into the synthesized peptide thus allowing formation of a loop in the peptide, said thioether bond being produced by reacting a sulfhydryl group in the synthesized peptide with an active alkyl group attached to an N^α-moiety or side chain of an amino acid or peptide, said amino acid or peptide being coupled to the synthesized peptide by the thioether bond.

6. The method according to claim 1 in which the solid support is 1% cross-linked chloromethylated copolystyrene/divinylbenzene resin.

7. The method according to claim 6 in which the resin-bound thiol compound is

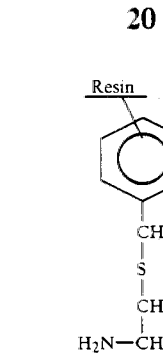

8. The method according to claim 6 in which the resin-bound thiol compound is

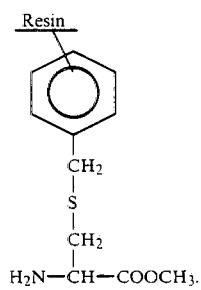

9. The method according to claim 6 in which the resin-bound thiol compound is

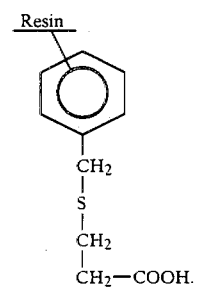

10. A benzylthioether-linked solid support-bound thiol compound having the formula

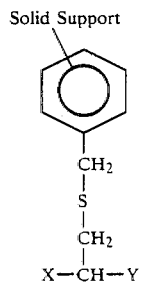

wherein X is H, NH₂,

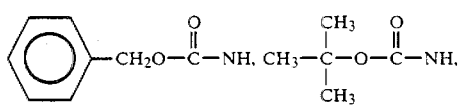

or acyl-NHY, said acyl being an amino acid or a peptide; Y is H, COOH, CONHNH₂,

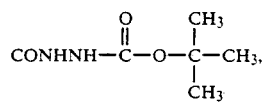

the ester COOR¹ in which R¹ is selected from the group consisting of methyl, ethyl, phenyl, ortho-nitrophenyl and para-nitrophenyl, the amide CONH₂, or the amide CONHR² in which R² is an amino acid or peptide; and providing that X and Y cannot both be H.

11. A benzylthioether-linked solid support-bound thiol compound of formula

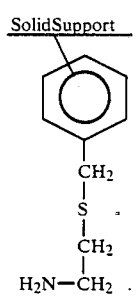

12. A benzylthioether-linked solid support-bound thiol compound of formula

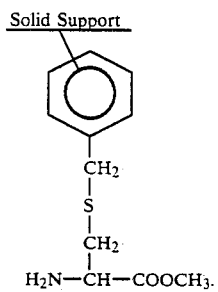

13. A benzylthioether-linked solid support-bound thiol compound of formula

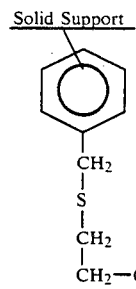

14. A compound according to any of claims 10–13 in which the solid support is 1% cross-linked chloromethylated copolystyrene/divinylbenzene resin.

15. An antigen comprising a synthesized peptide containing therein a C-terminal cysteamine wherein the C-terminal reactive group of the peptide is a free sulfhydryl group of said cysteamine, said synthesized peptide being conjugatable through the free sulfhydryl group to a carrier protein.

16. An anitgen comprising a synthesized peptide containing therein an N-terminal β-mercaptopropionic acid wherein the N-terminal reactive group of the peptide is a free sulfhydryl group of said β-mercaptopropionic acid, said synthesized peptide being conjugatable through the free sulfhydryl group to a carrier protein.

17. An antibody which specifically binds to an antigen comprising a synthesized peptide containing therein a C-terminal cysteamine wherein the C-terminal reactive group of the peptide is a free sulfydryl group of said cysteamine, said peptide being conjugatable through the free sulfhydryl group to a carrier protein such that upon immunization of a suitable host, the conjugate elicits production of the antibody.

18. An antibody which specifically binds to an antigen comprising a synthesized peptide containing therein an N-terminal β-mercaptopropionic acid wherein the N-terminal reactive group of the peptide is a free sulfhydryl group of said β-mercaptopropionic acid, said synthesized peptide being conjugatable through the free sulfhydryl group to a carrier protein such that upon immunization of a suitable host, the conjugate elicits production of the antibody.

19. A method for synthesizing a peptide according to claim 2, further comprising conjugating the peptide through the free sulfhydryl group of the peptide to a carrier protein.

UNITED STATES PATENT AND TRADEMARK OFFICE
CERTIFICATE OF CORRECTION

PATENT NO. : 4,786,684
DATED : November 22, 1988
INVENTOR(S) : John D. Glass

It is certified that error appears in the above-identified patent and that said Letters Patent is hereby corrected as shown below:

First page, 9th line of ABSTRACT, "regenertion" should read --regeneration--;

First page, 15th line of ABSTRACT, "acyl-NHY" should read --acyl-NH--;

Col. 1, line 33, "suora" should read --supra--;

Col. 2, line 8, "$\alpha$-NH" should read --$\alpha$-NH$_2$--;

Col. 2, line 39, "sucra" should read --supra--;

Col. 6, line 15, "presesnt" should read --present--;

Col. 6, line 47, "sulfydryl" should read --sulfhydryl--;

Col. 6, line 61, "sulhydryl" should read --sulfhydryl--;

UNITED STATES PATENT AND TRADEMARK OFFICE
CERTIFICATE OF CORRECTION

PATENT NO. : 4,786,684

DATED : November 22, 1988

INVENTOR(S) : John D. Glass

It is certified that error appears in the above-identified patent and that said Letters Patent is hereby corrected as shown below:

Col. 6, line 63, "sulhydryl" should read --sulfhydryl--;

Col. 8, line 26, "sulfydryl" should read --sulfhydryl--;

Col. 8, line 61, "sulfydryl" should read --sulfhydryl--;

Col. 9, line 12, after "moiety." insert --The--;

Col. 9, line 15, "$N^G p-$" should read --$N^G-p-$--

Col. 9, line 21, after "mixture" insert --was--;

Col. 11, line 22, "$No_2$" should read --$NO_2$--;

Col. 12, line 13, "sulhydryl" should read --sulfhydryl--;

Col. 13, line 25, "H:835" should read --H:8.35--;

Col. 13, line 40, "β-mercapto-" should start a new paragraph;

Col. 15, line 37, after "previous" insert --example.--;

UNITED STATES PATENT AND TRADEMARK OFFICE
CERTIFICATE OF CORRECTION

PATENT NO. : 4,786,684
DATED : November 22, 1988
INVENTOR(S) : John D. Glass

It is certified that error appears in the above-identified patent and that said Letters Patent is hereby corrected as shown below:

Col. 17, line 31, "phe" should read --Phe--;

Col. 17, line 49, after "$CH_2$-" (last occ.), insert --CO- --;

Col. 18, line 67, "benzlhioether-linked" should read --benzylthioether-linked--; and Col. 22, line 32, "sulfydryl" should read --sulfhydryl--.

Signed and Sealed this

Sixteenth Day of May, 1989

Attest:

DONALD J. QUIGG

Attesting Officer

Commissioner of Patents and Trademarks